United States Patent
Vos

(10) Patent No.: US 11,318,049 B2
(45) Date of Patent: May 3, 2022

(54) GOGGLE

(71) Applicant: VOG—IMAGE POLICE INC., Taichung (TW)

(72) Inventor: Gavin Michael Vos, Taichung (TW)

(73) Assignee: VOG—IMAGE POLICE INC., Taichung (TW)

( * ) Notice: Subject to any disclaimer, the term of this patent is extended or adjusted under 35 U.S.C. 154(b) by 0 days.

(21) Appl. No.: 16/651,112

(22) PCT Filed: Oct. 23, 2018

(86) PCT No.: PCT/CN2018/111340
§ 371 (c)(1),
(2) Date: Mar. 26, 2020

(87) PCT Pub. No.: WO2020/082222
PCT Pub. Date: Apr. 30, 2020

(65) Prior Publication Data
US 2021/0015669 A1      Jan. 21, 2021

(51) Int. Cl.
*A61F 9/02*      (2006.01)
(52) U.S. Cl.
CPC .............. *A61F 9/025* (2013.01); *A61F 9/029* (2013.01)
(58) Field of Classification Search
CPC ............. A61F 9/025; A61F 9/029; A42B 3/26
USPC ................................................ 2/9, 431, 438
See application file for complete search history.

(56) References Cited

U.S. PATENT DOCUMENTS

| 4,428,081 | A |   | 1/1984 | Smith |
|---|---|---|---|---|
| 4,542,538 | A | * | 9/1985 | Moretti ............... A62B 18/082 2/205 |
| 2012/0023647 | A1 |   | 2/2012 | Park |
| 2014/0157496 | A1 |   | 6/2014 | Ginter et al. |

FOREIGN PATENT DOCUMENTS

| CN | 103941854 A |   | 7/2014 |   |
|---|---|---|---|---|
| CN | 205750163 U |   | 11/2016 |   |
| CN | 106646921 A | * | 5/2017 | ............. A61F 9/025 |
| CN | 106646921 A |   | 5/2017 |   |
| WO | WO 2017189130 A1 |   | 11/2017 |   |

* cited by examiner

*Primary Examiner* — F Griffin Hall
(74) *Attorney, Agent, or Firm* — Muncy, Geissler, Olds & Lowe, P.C.

(57) ABSTRACT

A goggle includes a goggle frame, a lens assembly including a lens mounted on the goggle frame, two reels rotatably mounted on the goggle frame on opposing left and right ends of the lens and a soft sheet mounted between the two reels and abutting the outer surface of the lens, and a control assembly that can be set on one of the two reels according to the dominant hand of the wearer. With this, once the soft sheet is dirty, the wearer operates the control assembly with his dominant hand, so that the control assembly drives the reel set to rotate. At this time, the driven reel will further drive the soft sheet to move laterally relative to the lens, and then roll up the dirty part, so that the soft sheet can always be kept clean in the part corresponding to the lens.

5 Claims, 11 Drawing Sheets

GOGGLE

BACKGROUND OF THE INVENTION

1. Field of the Invention

The present invention relates to goggle technology and more particularly, to such a goggle that can be operated by either the left hand or the right hand to achieve the effect of cleaning the lens.

2. Description of the Related Art

For athletes involved in outdoor high-speed sports (such as skiing or off-road racing), in order to prevent the eyes from being injured by foreign objects (such as rain, wind, snow, mud or dust, etc.), goggle is generally worn to achieve eye protection. However, during the exercise, some foreign objects (such as snow or mud) are easily attached to the lens and affect the sight. As a result, athletes must constantly remove the attached foreign objects from the lens with their hands. It is also prone to danger. But this manner is not only quite troublesome, it is also prone to danger.

In order to solve the aforementioned problems, some goggles have been specially designed so that athletes can remove the attached foreign objects from the lens without using their hands. For example, as disclosed in the U.S. Patent Publication No. 2014/0157496, an eyewear, such as a goggle is provided with a film in front of the lens. Once a foreign body adheres to the film and affects the line of sight, the wearer can use a scroll mechanism to scroll the film. On the one hand, the dirty part is rolled up, and on the other hand, the clean part is released, so that the film in front of the lens can always be kept clean. However, the scroll mechanism of the aforementioned published patent can only be operated by the right-handed wearer, and the left-handed person can only adapt to it.

SUMMARY OF THE INVENTION

The present invention has been accomplished under the circumstances in view. It is the main object of the present invention to provide a goggle, which can be operated by users with different dominant hands, so that the lens can be kept in a clean state. The goggle provided by the present invention can be interchanged left and right according to the dominant hand of the wearer, so that the wearers of different dominant hands can operate smoothly. The wearer operates the control assembly with his or her dominant hand, on the one hand, to roll up the dirty part of the soft sheet, and on the other hand, to release the non-dirty part of the soft sheet. In this way, the soil sheet can always be kept clean in the part corresponding to the lens, so that the wearer can maintain a good line of sight during high-speed outdoor sports.

To achieve this and other objects of the present invention, a goggle comprises a goggle frame, a lens assembly, and a control assembly. The lens assembly comprises a lens, two opposite reels and a soft sheet. The lens is mounted on the goggle frame. The two reels are rotatably mounted in the goggle frame at opposing left and right ends of the lens. The soft sheet partially abuts against an outer surface of the lens, having two opposite ends thereof respectively wound around the two reels. The control assembly is detachably and selectively connected to one reel of the lens assembly, so that the control assembly can be interchanged left and right according to the wearer's dominant hand.

It can be known from the above that, once the outer surface of the soft sheet is dirty and affects the wearer's sight, the wearer first operates the control assembly with his or her dominant hand, so that the control assembly drives the connected reel to rotate. With this, the reel driven by the ratchet wheel can start to roll the soil sheet, so that the soft sheet moves laterally relative to the lens. On the one hand, the dirty part of the soft sheet is rolled up, and on the other hand, the clean part of the soft sheet is released. In this way, the soft sheet can always be kept clean in the part corresponding to lens.

Preferably, the control assembly comprises a casing, a ratchet wheel, a pawl, a rope wheel, a pulling rope, a finger rod and an elastic member. The casing is detachably mounted to the goggle frame, comprising an accommodation space, a shaft hole in communication with the accommodation space vertically and a rope hole in communication with the accommodation space laterally. The ratchet wheel is rotatably mounted in the accommodation space of the casing, comprising a transmission shaft. The transmission shaft is inserted through the shaft hole of the casing and detachably connected to one reel. The pawl is disposed in the casing and unidirectionally engaged with the ratchet wheel to limit the ratchet wheel for unidirectional rotation. The rope wheel is rotatably mounted in the accommodation space of the casing for rotating the ratchet wheel unidirectionally. The pulling rope is inserted through the rope hole of the casing, The pulling rope has one end thereof connected to the rope wheel and an opposite end thereof connected to the finger rod, so that on the one hand, the pulling rope can be driven by the finger rod to drive the rope wheel to rotate, on the other hand, the pulling rod can be pulled to reset by the rotation of the rope wheel. The elastic member acts on the rope wheel to drive the rope wheel to wind up the pulling rope. By this, when the wearer manually pulls the finger rod with the dominant hand, the finger rod drives the rope wheel to rotate through the pulling rope, and then the rope wheel drives the ratchet wheel to rotate, and then the ratchet wheel drives the connected reel to rotate, so that a reel driven by the ratchet wheel further drives the soft sheet to move laterally relative to the lens. Conversely, once the finger rod is released, the rope wheel will be driven by the resetting force of the elastic member to roll up the pulling rope, so that the pulling rope will drive the finger rod to complete the reset. As for the ratchet wheel, it is restricted by pawl at this time and remains stationary.

Preferably, the goggle frame comprises a frame body and two opposite side covers. The frame body comprises a fastening groove at a bottom surface of each of opposing left and right ends thereof. The two side covers are respectively detachably mounted on opposing left and right ends of the frame body. The two reels are respectively rotatably mounted at the opposing left and right ends of the frame body and covered by one respective side cover. The casing comprises a first fastening portion located at a top side thereof. The control assembly further comprises a bottom cover. The top surface of the bottom cover is provided with a second fastening portion. The first fastening portion of the casing is detachably fastened to one fastening groove of the frame body. The second fastening portion of the bottom cover is detachably fastened to the other fastening groove of the frame body. With this, after removing the two side covers from the frame body, the position of the control assembly can be adjusted according to the wearer's dominant hand.

Other advantages and features of the present invention will be fully understood by reference to the following

DETAILED DESCRIPTION OF THE INVENTION

Figure 1:
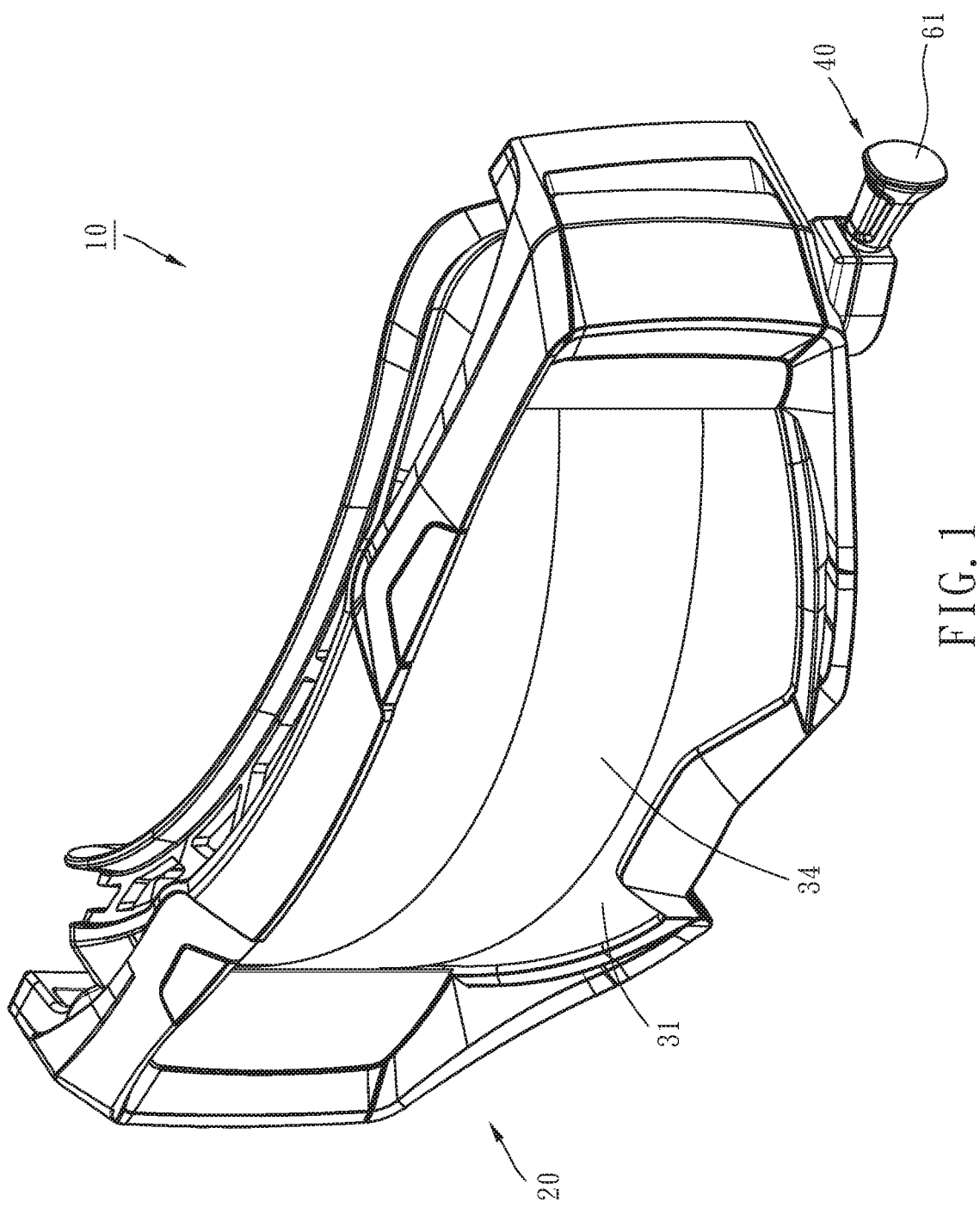
FIG. 1 is an oblique top elevational view of a goggle in accordance with the present invention.

The applicant first explains here that in the embodiment and drawings to be described below, the same reference numerals represent the same or similar elements or their structural features.

Figure 2:
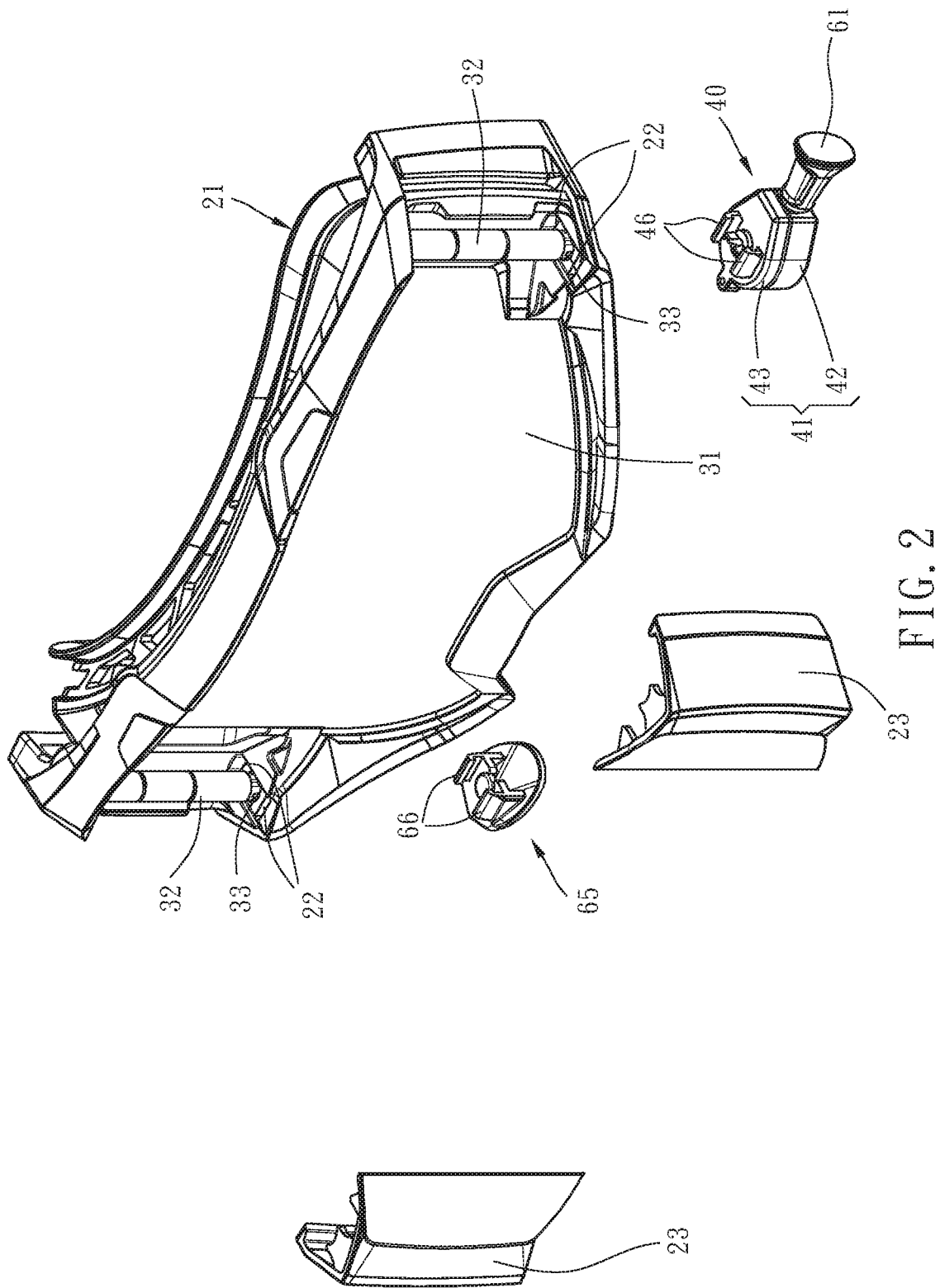
FIG. 2 is an exploded view of a part of the goggle in accordance with the present invention.
Figure 3:
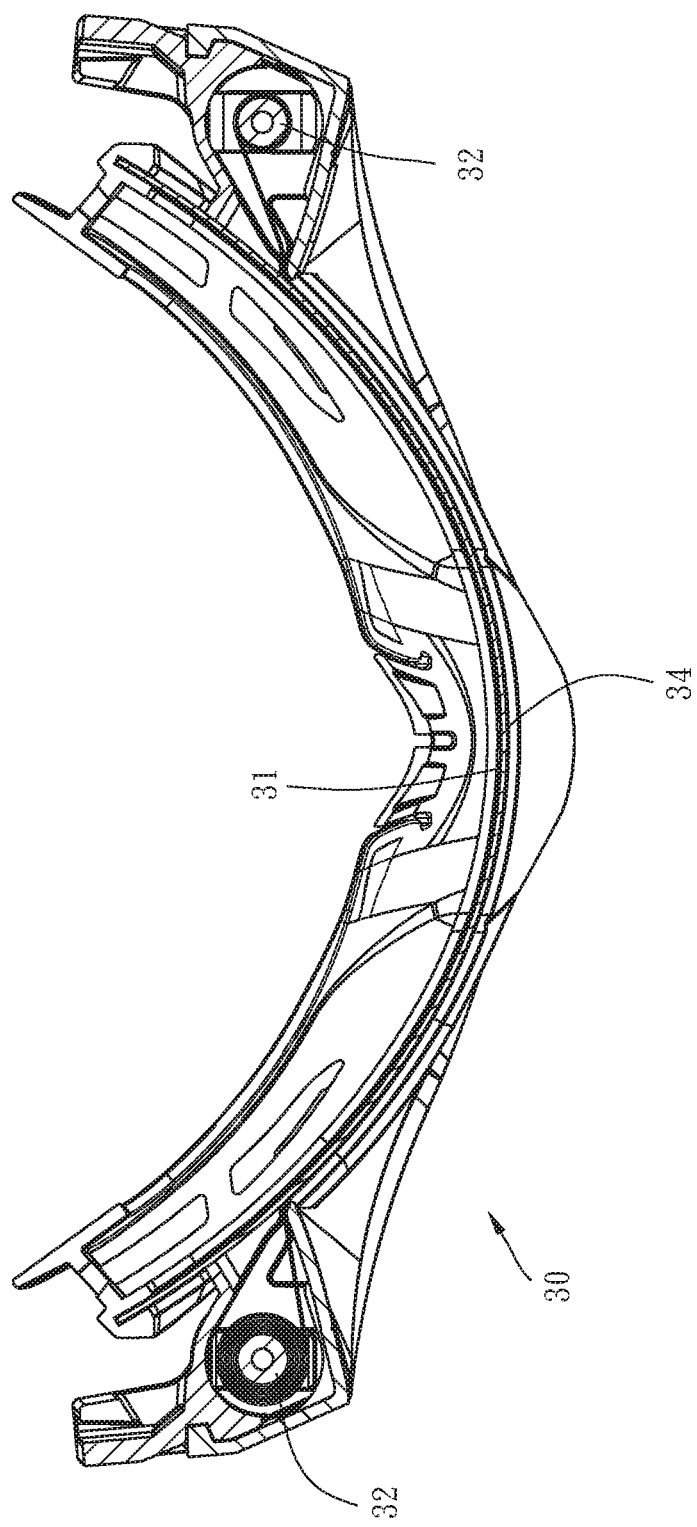
FIG. 3 is a sectional top view of the goggle in accordance with the present invention.

Referring to FIGS. 1-3, a goggle 10 in accordance with the present invention comprises a goggle frame 20, a lens assembly 30, and a control assembly 40.

The goggle frame 20 comprises a frame body 21 and two opposite side covers 23. The bottom surfaces of the left and right ends of the frame body 21 are respectively provided with a fastening groove 22 (see FIG. 2). The two side covers 23 are assembled at the left and right ends of the frame body 21 in a snap-fit manner.

Figure 5:
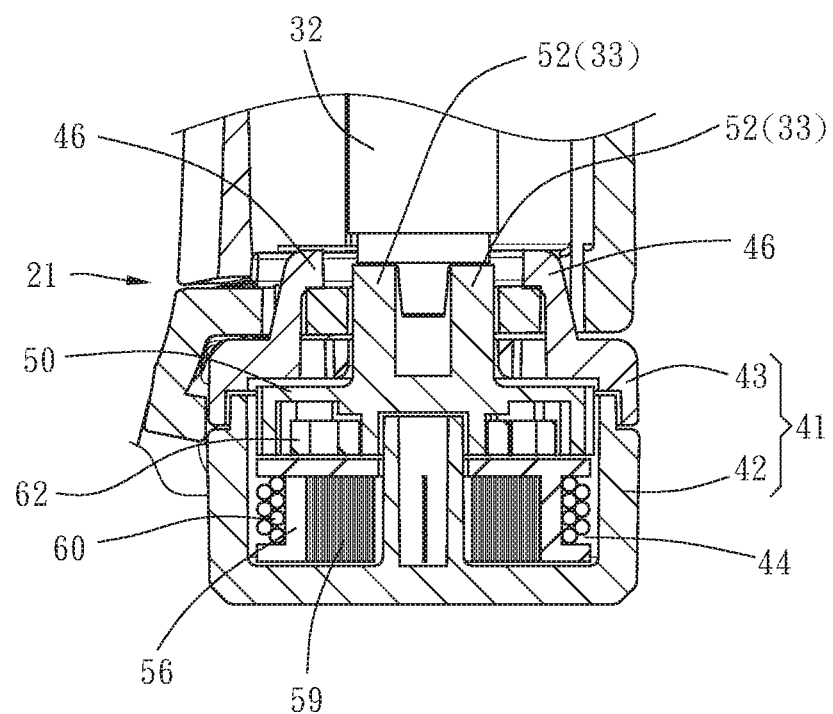
FIG. 5 is a sectional assembly view of the goggle frame, reel and control assembly of the goggle in accordance with the present invention.
Figure 6:
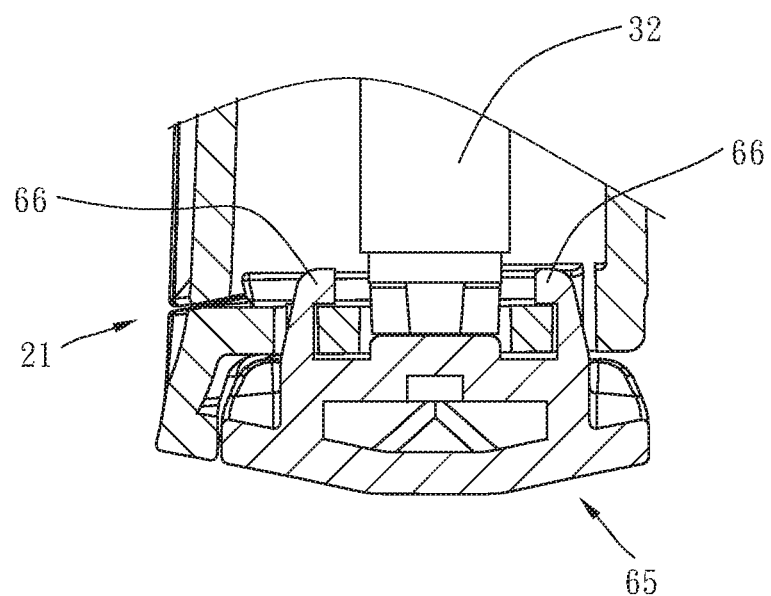
FIG. 6 is a sectional assembly view of the goggle frame, reel and bottom cover of the goggle in accordance with the present invention.

As shown in FIG. 2 and FIG. 3, the lens assembly 30 comprises a lens 31, two opposite reels 32, and a soft sheet 34. The lens 31 is fixed on the frame body 21 of the goggle frame 20. The two reels 32 are assembled at the left and right ends of the frame body 21 of the goggle frame 20 and respectively covered by the side covers 23 of the goggle frame 20. The bottom ends of the two reels 32 respectively have two opposite engaging recesses 33 (as shown in FIGS. 2, 5 and 6). The soft sheet 34 is made of a light-transmissive material, a part of the soft sheet 34 abuts on the outer surface of the lens 31, and two opposite ends of the soft sheet 34 are respectively wound around the two reels 32 (as shown in FIGS. 1 and 3). In this way, one of the reels 32 can roll up the soft sheet 34 when it is rotated, so that the soft sheet 34 moves laterally relative to the lens 31. During the lateral movement of the soft sheet 34, the other reel 32 will be synchronized to rotate.

Figure 4:
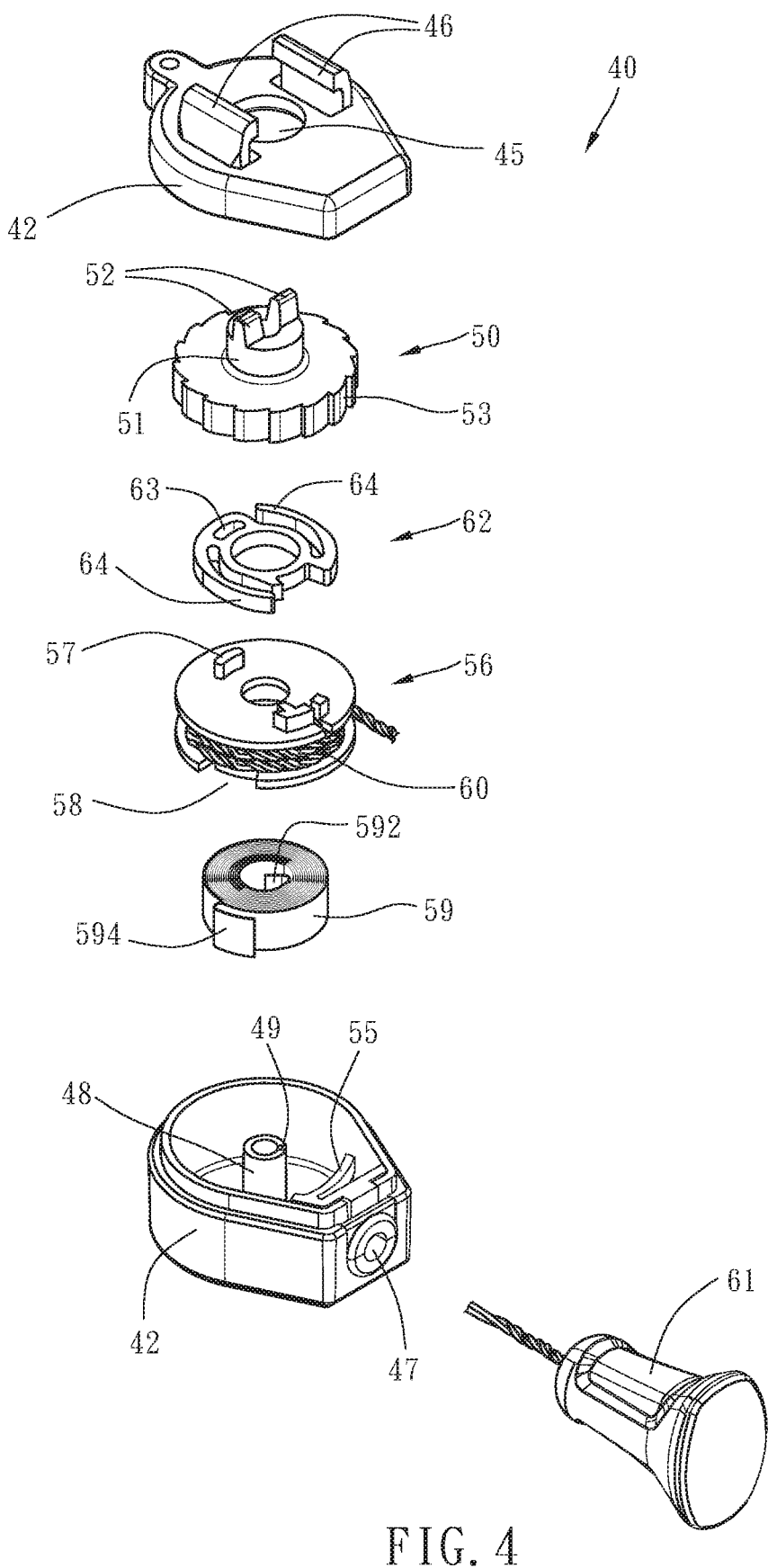
FIG. 4 is an exploded view of the control assembly of the goggle in accordance with the present invention.

The control assembly 40 comprises a casing 41, a ratchet wheel 50, a pawl 55, a rope wheel 56, an elastic member 59, a pulling rope 60, a finger rod 61, a transmission plate 62, and a bottom cover 65, as shown in FIGS. 2 and 4.

The casing 41 comprises a holder base 42 and a top cover 43. The top cover 43 is provided on the top surface of the holder base 42 and forms an accommodation space 44 between the holder base 42 (see FIG. 5). The top cover 43 has a shaft hole 45 that communicates with the accommodation space 44 vertically, and a first fastening portion 46 at the top side thereof. The first fastening portion 46 of the casing 41 is fastened to one fastening groove 22 of the frame body 21 of the goggle frame 20, as shown in FIGS. 2 and 5, so that the two are assembled together in a detachable manner. The holder base 42 has a rope hole 47 located at one side thereof and laterally disposed in communication with the accommodation space 44, and a wheel shaft 48 disposed therein corresponding to the shaft hole 45. The wheel shaft 48 has a first engaging groove 49.

Figure 8A:
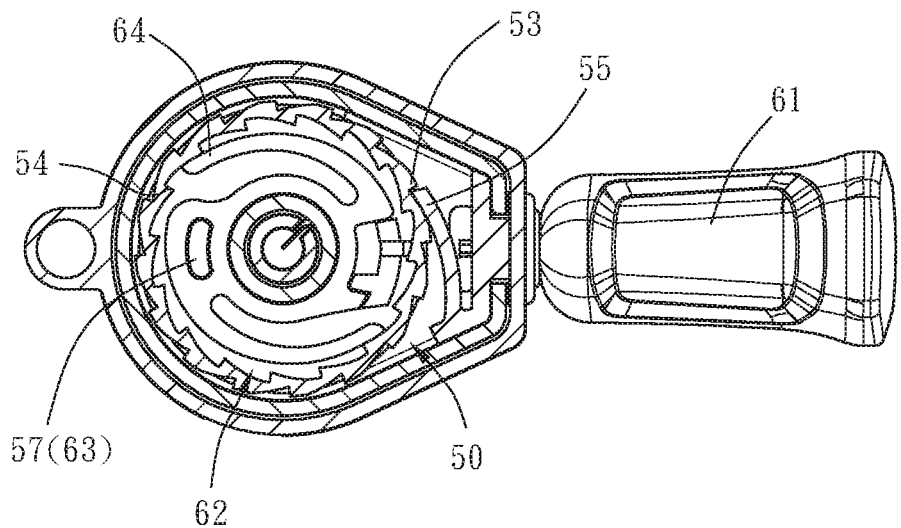
FIG. 8a is a sectional top view of the control assembly of the goggle in accordance with the present invention.
Figure 11A:
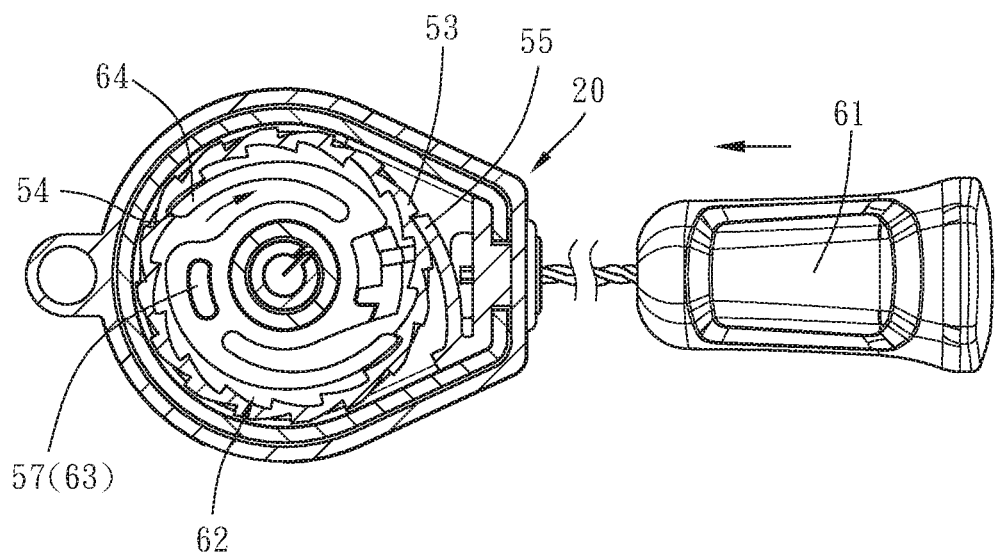
FIG. 11a is similar to FIG. 10a, illustrating the transmission plate reversely rotated and the ratchet wheel stopped by the pawl.

The ratchet wheel 50 is mounted in the accommodation space 44, having a top side thereof provided with a transmission shaft 51. The transmission shaft 51 of the ratchet wheel 50 is inserted through the shaft hole 45 of the casing 41, and provided with two opposite engaging protrusions 52. The engaging protrusions 52 of the ratchet wheel 50 are detachably fastened to the engaging recesses 33 of one reel 32, so that the ratchet wheel 50 can drive the connected reel 32 to rotate. In addition, as shown in FIG. 8a, the outer perimeter of the ratchet wheel 50 is provided with an outer ring tooth portion 53, and the inner perimeter of the ratchet wheel 50 is provided with an inner ring tooth portion 54. The pawl 55 is set in the holder base 42 of casing 41 and is unidirectionally engaged with the outer ring tooth portion 53 of the ratchet wheel 50, as shown in FIG. 4 and FIG. 11a, to limit the ratchet wheel 50 to unidirectional rotation.

The rope wheel 56 is mounted in the accommodation space 44 and rotatably coupled to the wheel shaft 48 of the casing 41. The rope wheel 56 has a driving protrusion 57 located at a top side thereof, and a second engaging groove 58 located at one lateral side thereof.

The elastic member 59 in this embodiment is a coil spring. The elastic member 59 has an inner end 592 thereof fastened to the first engaging groove 49 of the wheel shaft 48 of the casing 41 and an outer end 594 thereof fastened to the second engaging groove 58 of the rope wheel 56, for providing a spring force to drive the rope wheel 56 for reverse rotation (as shown by the arrow in FIG. 11b).

The pulling rope 60 is inserted through the rope hole 47 of the casing 41 with one end thereof disposed in the accommodation space 44 and connected to the rope wheel 56 and an opposite end thereof disposed outside the accommodation space 44 and connected to the finger rod 61, so that on the one hand, the pulling rope 60 can be pulled by the finger rod 61 to drive the rope wheel 56 to rotate forward (as shown by the arrow in FIG. 10b), on the other hand, the pulling rope 60 can be reversed by the rope wheel 56 (as shown by the arrow in FIG. 11b) to carry the finger rod 61 in direction toward the casing 41.

Figure 10A:
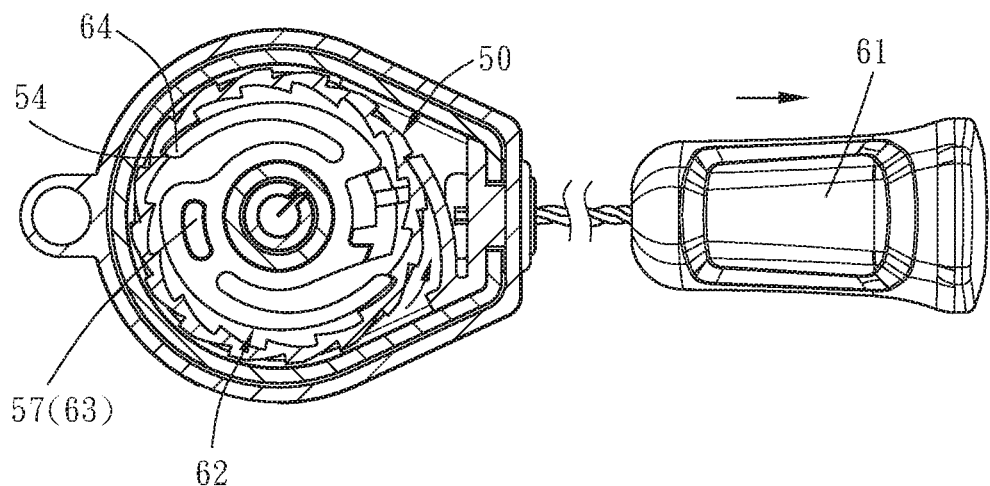
FIG. 10a is similar to FIG. 8a, illustrating the ratchet wheel rotated forward.

The transmission plate 62 is provided between the ratchet wheel 50 and the rope wheel 56, and has a transmission recess 63. The transmission recess 63 of the transmission plate 62 is engaged with the driving protrusion 57 of the rope wheel 56, so that the transmission plate 62 can be synchronized with the rope wheel 56. In addition, the transmission plate 62 has two opposite ratchet portions 64. When the rope wheel 56 rotates forward in the direction of the arrow shown in FIG. 10b, the ratchet portion 64 of the transmission plate 62 will engage the inner ring tooth portion 54 of the ratchet wheel 50, as shown in FIG. 10a, so that the ratchet wheel 50 rotates with the rope wheel 56. When the rope wheel 56 rotates reversely in the direction of the arrow as shown in FIG. 11b, the ratchet portion 64 of the transmission plate 62 will not engage the inner ring tooth portion 54 of the ratchet wheel 50, as shown in FIG. 11a, so that the ratchet wheel 50 does not rotate with the rope wheel 56.

The top surface of the bottom cover 65 is provided with a second fastening portion 66. The second fastening portion 66 of the bottom cover 65 is fastened to the other fastening groove 22 of the frame body 21 of the goggle frame 20, as shown in FIG. 2 and FIG. 6, so that the two are assembled together in a detachable manner.

Figure 7:
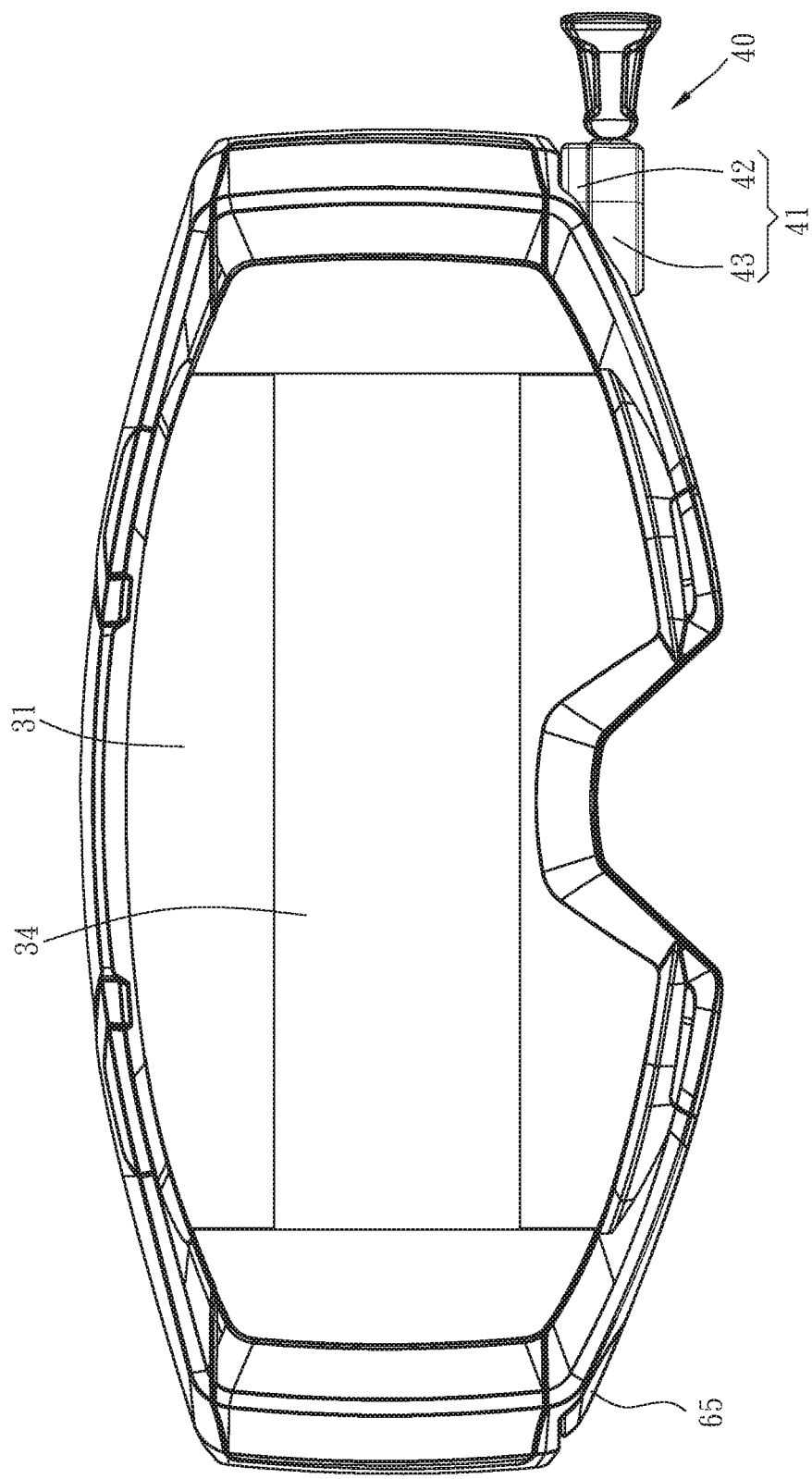
FIG. 7 is a front view of the goggle in accordance with the present invention, mainly illustrating the control assembly mounted to the left end of the goggle frame.
Figure 12:
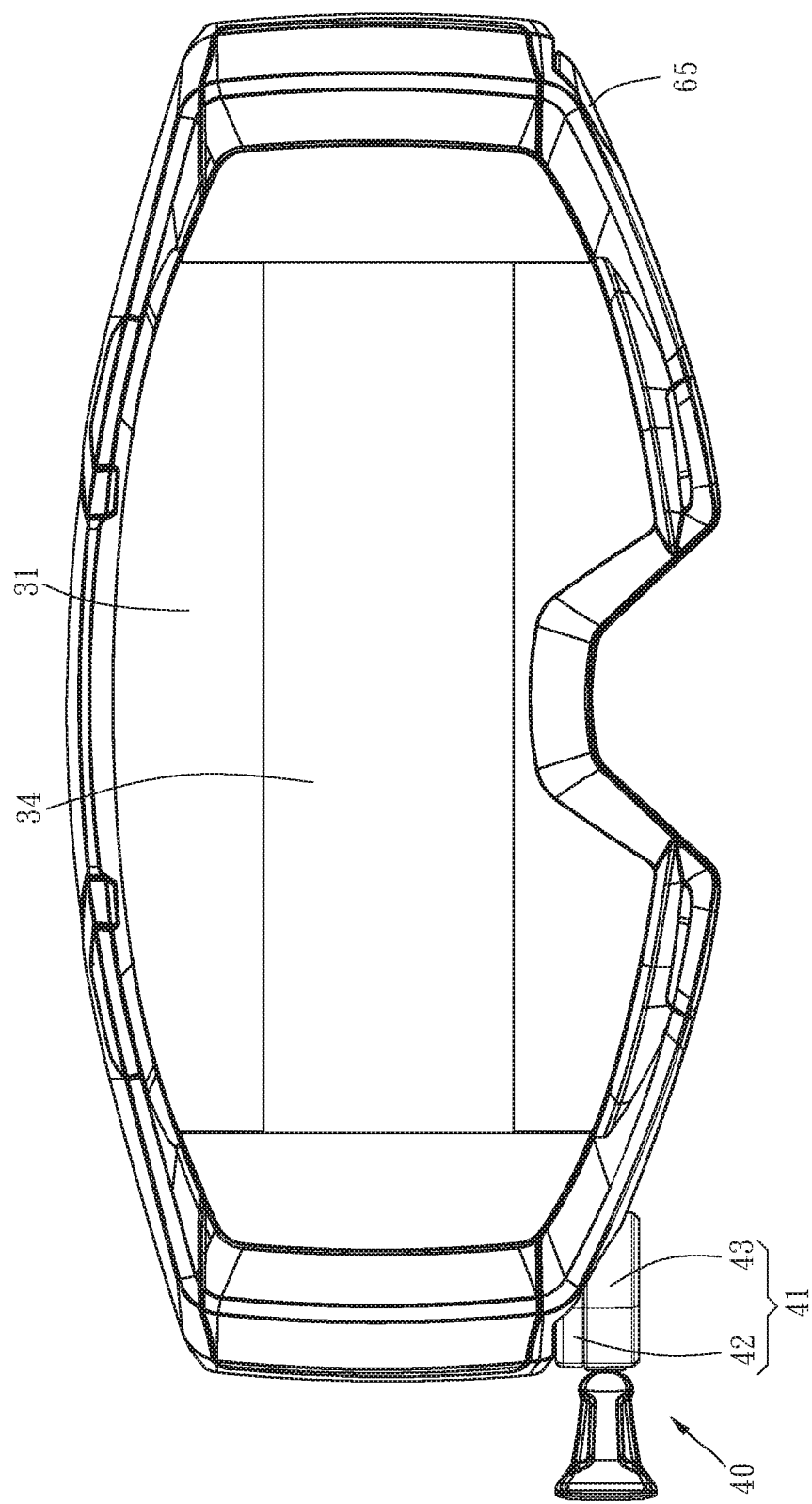
FIG. 12 is similar to FIG. 7, mainly illustrating the control assembly mounted to the right end of the goggle frame.

It can be known from the above, before starting to use, adjust the position of the control assembly 40 according to the dominant hand of the wearer. When adjusting, first detach the two side covers 23, and then release the fastening relationship between casing 41 and frame body 21 of the goggle frame 20 and the fastening relationship between the bottom cover 65 and the frame body 21 of the goggle frame 20 in order to detach the control assembly 40 and the bottom cover 65. Then choose the installation position of the two according to the dominant hand of the wearer. For example, if the wearer's dominant hand is the right hand, as shown in FIG. 12, assemble the control assembly 40 at the right end of the goggle frame 20 and the bottom cover 65 at the left end of the goggle frame 20 through the casing 41. On the contrary, if the wearer's dominant hand is the left hand, as shown in FIG. 7, assemble the control assembly 40 at the left end of the goggle frame 20 and the bottom cover 65 at the right end of the goggle frame 20 through the casing 41. After determining the installation position of the two, reinstall the two side covers 23 and start using.

Figure 8B:
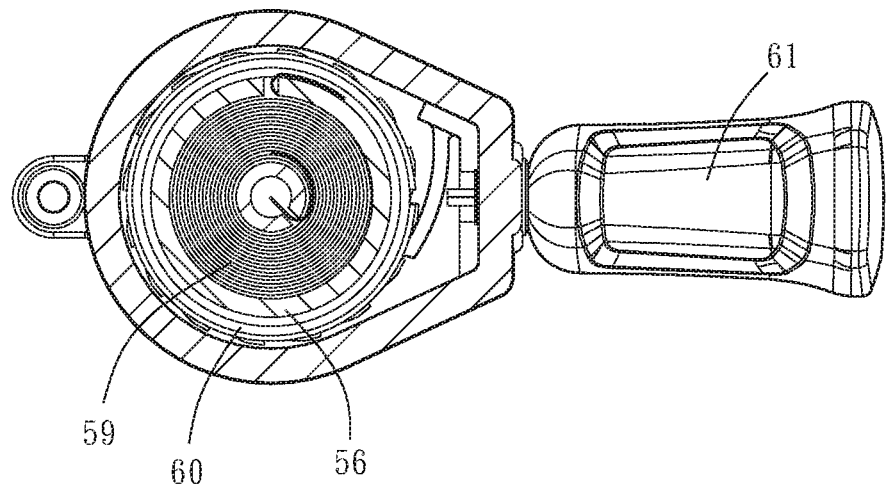
FIG. 8b is a sectional bottom view of the control assembly of the goggle in accordance e present invention.
Figure 9:
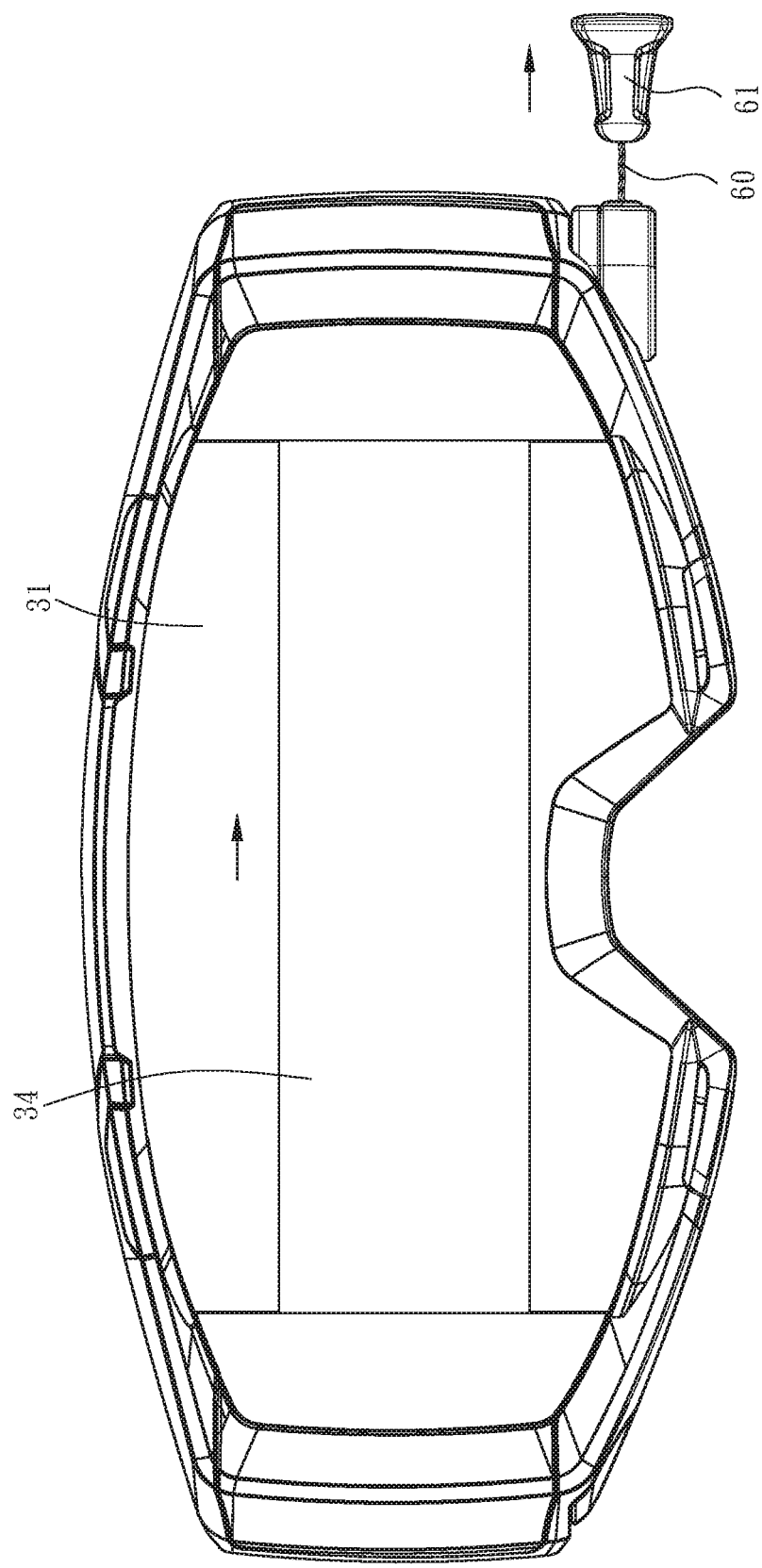
FIG. 9 is similar to FIG. 7, illustrating the finger rod pulled outwards.
Figure 10B:
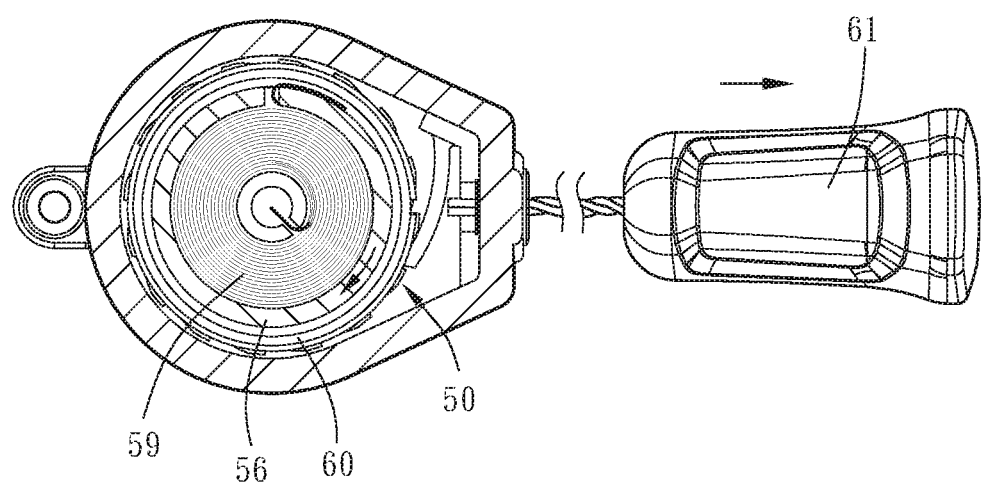
FIG. 10b is similar to FIG. 8b, illustrating the rope wheel rotated forward.
Figure 11B:
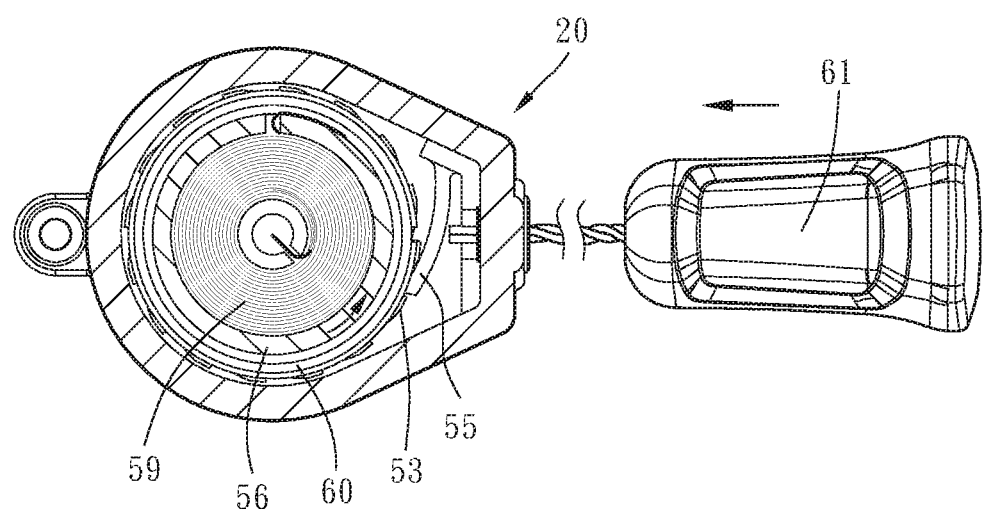
FIG. 11b is similar to FIG. 10b, illustrating the rope wheel reversed.

During the use, when the outer surface of the soft sheet 34 is dirty and affects the sight, the wearer pulls the finger rod 61 by his or her dominant hand, as shown in FIG. 9, so that the finger rod 61 drives the rope wheel 56 to rotate forward in the direction of the arrow shown in FIG. 10b through the pulling rope 60. At this time, the rope wheel 56 will, on the one hand, roll the elastic member 59 to accumulate the elastic restoring force of the elastic member 59, and on the other hand, drive the ratchet wheel 50 to rotate together through the transmission plate 62 (as shown in FIG. 10a). Then, the ratchet wheel 50 drives the connected reel 32 to rotate together. With this, the reel 32 driven by the ratchet wheel 50 can start to roll the soft sheet 34, so that the soft sheet 34 moves laterally relative to the lens 31. On the one hand, the dirty part of the soft sheet 34 is rolled up, and on the other hand, the clean part of the soft sheet 34 is released. In this way, the soft sheet 34 can always be kept clean in the part corresponding to lens 31. Release the finger rod 61 after removing dirt. At this time, the rope wheel 56 will be subject to the resetting force of the elastic member 59 to rotate reversely in the direction of the arrow shown in FIG. 11b, and at the same time, the pulling rope 60 will be rolled up. The pulling rope 60 will further drive the finger rod 61 to reset until one end of the finger rod 61 abuts against the holder base 42 of the casing 41 (as shown in FIGS. 8a and 8b). As for the ratchet wheel 50, it is restricted by pawl 55 at this time and remains stationary.

In summary, the goggle 10 of the present invention allows the wearer to change the position of the control assembly 40 according to his or her dominant hand, so that the wearers of different dominant hands can operate smoothly. During operation, the soft sheet 34 is quickly scrolled by using the cooperation of the ratchet wheel 50 and the pawl 55, so that the wearer can maintain a good line of sight during outdoor high-speed sports.

Of course, there can be many other embodiments of the present invention. Without departing from the spirit and scope of the present invention, those skilled in the art can make various corresponding changes and modifications according to the present invention, but these corresponding changes and modifications should fall within the protection scope of the claims attached to the present invention.

What is claimed is:

1. A goggle, comprising:
   a lens assembly comprising a lens, two opposite reels and a soft sheet, said lens being mounted on said goggle frame, said two reels being rotatably mounted in said goggle frame at opposing left and right ends of said lens, said soft sheet being partially abutted against an outer surface of said lens and having two opposite ends thereof respectively wound around said two reels; and
   a control assembly detachably and selectively connected to one said reel of said lens assembly and used to drive the connected said reel to rotate, so that the said reel driven by said control assembly drives said soft sheet to move laterally relative to said lens, wherein said control assembly is configured to enable a right handed user to disassemble said control assembly from the reel that is mounted at the left end of said lens and assemble said control assembly at the reel that is mounted at said right end of said lens, and to enable a left handed user to disassemble said control assembly from the reel that is mounted at the right end of said lens and assemble said control assembly at the reel that is mounted at said left end of said lens;
   wherein said control assembly comprises a casing, a ratchet wheel, a pawl, a rope wheel, a pulling rope, a finger rod and an elastic member, said casing being detachably mounted to said goggle frame, said casing comprising an accommodation space, a shaft hole in communication with said accommodation space vertically and a rope hole in communication with said accommodation space laterally, said ratchet wheel being rotatably mounted in said accommodation space of said casing and comprising a transmission shaft, said transmission shaft being inserted through said shaft hole of said casing and detachably connected to one said reel, said pawl being disposed in said casing and unidirectionally engaged with said ratchet wheel to limit said ratchet wheel for unidirectional rotation, said rope wheel being rotatably mounted in said accommodation space of said casing for rotating said ratchet wheel unidirectionally, said pulling rope being inserted through said rope hole of said casing, said pulling rope having one end thereof connected to said rope wheel and an opposite end thereof connected to said finger rod, said elastic member acting on said rope wheel to drive said rope wheel to wind up said pulling rope;
   wherein said ratchet wheel comprises an outer ring tooth portion located on an outer perimeter thereof and an inner ring tooth portion located on an inner perimeter thereof, said pawl is unidirectionally engaged with said outer ring tooth portion of said ratchet wheel; said control assembly further comprises a transmission plate connected to said rope wheel, said transmission plate comprising a ratchet portion unidirectionally engaged with said inner ring tooth portion of said ratchet wheel.

2. The goggle as claimed in claim 1, wherein each said reel comprises an engaging recess located at a bottom side thereof; said transmission shaft of said ratchet wheel comprises an engaging protrusion detachably engaging in said engaging recess of one said reel.

3. The goggle as claimed in claim 1, wherein said transmission plate comprises a transmission recess; said rope wheel comprises a driving protrusion located at a top surface thereof and engaged with said transmission recess of said transmission plate.

4. The goggle as claimed in claim 1, wherein said goggle frame comprises a frame body and two opposite side covers, said frame body comprising a fastening groove at a bottom surface of each of opposing left and right ends thereof, said two side covers being respectively detachably mounted on opposing left and right ends of said frame body; said lens is mounted on said frame body; said two reels are respectively rotatably mounted at the opposing left and right ends of said frame body and covered by one respective said side cover; said casing comprises a first fastening portion located at a top side thereof and detachably fastened to one said fastening groove of said frame body.

5. The goggle as claimed in claim 4, wherein said control assembly further comprises a bottom cover, said bottom cover comprises a second fastening portion located at a top surface thereof and detachably fastened to the other said fastening groove of said frame body.

\* \* \* \* \*